United States Patent
Schäfer et al.

(10) Patent No.: US 7,056,343 B2
(45) Date of Patent: Jun. 6, 2006

(54) EXTENDABLE SPINAL IMPLANT AND EXTENSION TOOL

(75) Inventors: Bernd Schäfer, Oberägeri (CH); Thilo Trautwein, Filderstadt (DE)

(73) Assignee: Bernd Schafer, Oberageri (CH)

( * ) Notice: Subject to any disclaimer, the term of this patent is extended or adjusted under 35 U.S.C. 154(b) by 0 days.

(21) Appl. No.: 10/476,811

(22) PCT Filed: Jan. 30, 2003

(86) PCT No.: PCT/EP03/00932

§ 371 (c)(1),
(2), (4) Date: Apr. 15, 2004

(87) PCT Pub. No.: WO03/073964

PCT Pub. Date: Sep. 12, 2003

(65) Prior Publication Data

US 2004/0172129 A1  Sep. 2, 2004

(30) Foreign Application Priority Data

Mar. 2, 2002 (DE) ............... 102 10 214

(51) Int. Cl.
*A61F 2/44* (2006.01)
(52) U.S. Cl. .................... 623/17.11
(58) Field of Classification Search ........... 623/17.11, 623/17.13, 17.15, 17.16, 17.12, 17.14, 23.47
See application file for complete search history.

(56) References Cited

U.S. PATENT DOCUMENTS

| | | | |
|---|---|---|---|
| 4,553,273 A | 11/1985 | Wu | |
| 5,236,460 A * | 8/1993 | Barber | 623/17.15 |
| 5,702,455 A * | 12/1997 | Saggar | 623/17.15 |
| 5,776,198 A * | 7/1998 | Rabbe et al. | 623/17.15 |
| 6,015,436 A * | 1/2000 | Schonhoffer | 623/17.16 |
| 6,190,414 B1 * | 2/2001 | Young et al. | 623/17.15 |
| 6,193,756 B1 * | 2/2001 | Studer et al. | 623/17.15 |
| 6,299,644 B1 * | 10/2001 | Vanderschot | 623/17.15 |
| 6,524,341 B1 * | 2/2003 | Lang et al. | 623/17.15 |
| 6,719,796 B1 * | 4/2004 | Cohen et al. | 623/17.15 |
| 6,752,832 B1 * | 6/2004 | Neumann | 623/17.15 |
| 2001/0056302 A1 * | 12/2001 | Boyer et al. | 623/17.15 |
| 2003/0163199 A1 * | 8/2003 | Boehm et al. | 623/17.11 |
| 2004/0049271 A1 * | 3/2004 | Biedermann et al. | 623/17.11 |

FOREIGN PATENT DOCUMENTS

| | | |
|---|---|---|
| DE | 44 23 257 C2 | 1/1996 |
| DE | 195 19 101 A1 | 11/1996 |
| DE | 198 16 782 A1 | 10/1999 |
| EP | 0 567 424 A1 | 10/1993 |
| EP | 0 950 388 A2 | 10/1999 |
| EP | 1 080 703 A3 | 3/2001 |
| WO | WO 98/44878 | 10/1998 |
| WO | WO 98/46173 A | 10/1998 |
| WO | WO/01 72246 A | 10/2001 |

\* cited by examiner

*Primary Examiner*—Eduardo C. Robert
*Assistant Examiner*—David Comstock
(74) *Attorney, Agent, or Firm*—Dierker & Associates, P.C.

(57) ABSTRACT

An extendable spinal implant has a first outer sleeve and a second outer sleeve coaxially disposed thereto. An inside drive element is connected by means of screws to at least one of the outer sleeves. The inside drive element has an outside thread, and the outer sleeve that is connected to the drive element has an inside thread that fits on the outside thread. The inside drive element rests on a supporting ring, and is rotatably driven with respect to the supporting ring.

15 Claims, 4 Drawing Sheets

EXTENDABLE SPINAL IMPLANT AND EXTENSION TOOL

BACKGROUND

The present disclosure relates generally to spinal implants, and more particularly to extendable spinal implants.

Spinal implants may serve as intervertebral implants to replace individual vertebrae, as is known, e.g., from U.S. Pat. No. 4,657,550. In this known intervertebral implant, a thread bolt is screwed into each end of a threaded sleeve, with the two front surfaces of the thread bolts facing away from each other and meshing with the buttressing bases which abut the vertebrae to be buttressed. When the threaded sleeve is turned by means of a radially insertable pin or by means of a hooked wrench, the two thread bolts having a right-hand thread and a left-hand thread are screwed out of or into the threaded sleeve. One disadvantage of this device is that the tool used for turning the threaded sleeve has to be removed and reinserted after it has made a certain turn, e.g., after a quarter turn. This may be quite difficult or even impossible in a great number of surgical interventions.

Thus, it would be desirable to provide a spinal implant, in particular an intervertebral implant, that may be more universally used and considerably more easily handled during implantation.

SUMMARY

An extendable spinal implant has a first outer sleeve and, coaxially disposed thereon, a second outer sleeve. An inside drive element is partially connected by means of screws to at least one of the outer sleeves, with the inside drive element having a first screw thread, e.g., an outside screw thread, and the outer sleeve that is screwed to the drive element having a second screw thread, e.g., an inside screw thread, that fits on the outside screw thread. The inside drive element rests on a supporting ring, and the drive element can be driven in the area of the front surface that faces the supporting ring.

BRIEF DESCRIPTION OF THE DRAWINGS

Objects, features and advantages of embodiments of the present disclosure will become apparent by reference to the following detailed description and drawings, in which like reference numerals correspond to similar, though not necessarily identical components. For the sake of brevity, reference numerals having a previously described function may not necessarily be described in connection with subsequent drawings in which they appear.

DETAILED DESCRIPTION

Figure 1:
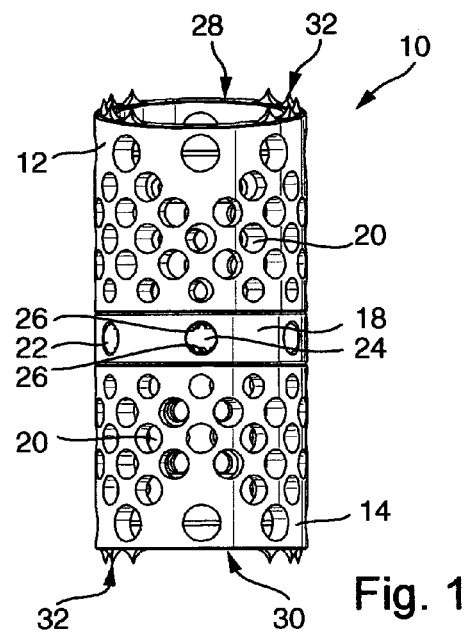
FIG. 1 is a perspective view of an embodiment of the extendable spinal implant according to the present disclosure.

An extendable spinal implant according to the present disclosure will be described generally immediately below; and more specifically further hereinbelow.

The extendable spinal implant of the present disclosure has a first outer sleeve and, coaxially disposed thereon, a second outer sleeve. An inside drive element is partially connected by means of screws to at least one of the outer sleeves, with the inside drive element having a first screw thread, e.g., an outside screw thread, and the outer sleeve that is screwed to the drive element having a second screw thread, e.g., an inside screw thread, that fits on the outside screw thread. The inside drive element rests on a supporting ring, and the drive element can be driven in the area of the front surface that faces the supporting ring.

The inside drive element preferably has two inner sleeves. According to an alternate embodiment, each inner sleeve is screwed into an outer sleeve. The front surfaces of the inner sleeves that face each other preferably are resting on a supporting ring which spaces the sleeves a certain distance apart from each other.

In the spinal implant according to the present disclosure, the two outer portions are formed by an outer sleeve, which has the advantage that, compared to the known device mentioned above, the outer sleeve supports the spinal implant over a larger supporting area on the facing vertebra. Thus, buttressing bases are not required. In addition, having the drive, in particular a bevel drive, located on the front surface makes it possible to avoid having to reinsert the tool after it has made a certain turn since the tool, in contrast to the known device, does not engage the circumference but rather the front surface of the drive element.

The drive element which is located between the two outer sleeves is preferably formed by two inner sleeves that are screwed into the two outer sleeves. The front surfaces of the inner sleeves that face each other rest on a supporting ring and are spaced a certain distance apart by means of the ring. The two inner sleeves can be driven in the area of their front surface, thus making it possible to screw them into and out of the outer sleeve. Since the two inner sleeves are spaced a certain distance apart, the two front surfaces can be accessed by means of the tool and can be turned without having to repeatedly reinsert the tool. As stated earlier, that is a problem with the known device mentioned earlier as described in U.S. Pat. No. 4,657,550 where the central element has to be turned by means of a pin or a hooked wrench.

An alternate embodiment of the present disclosure provides for the front surface of the inner sleeve to have teeth, in particular, half of a pair of bevel teeth. By way of these teeth, the inner sleeve or the inner sleeves can be turned by means of a suitable tool, e.g., by means of the mating part of the bevel teeth, so as to carry out the screwing motion.

The supporting ring preferably has at least one radial opening. The opening allows insertion of the tool into the supporting ring and to move it to the front surface of the inner sleeve, on the one hand, and to guide and support the tool, on the other hand. During surgical interventions, a guided and supported tool may pose a much lower risk than an unguided and unsupported tool.

To hold and support the inner sleeves, the supporting ring according to the present disclosure has a shoulder which projects radially inwardly and which serves as a support for the front surface of the inner sleeve. This shoulder does not necessarily run along the entire circumference of the inside surface of the supporting ring, it suffices if enough segments are provided which support the sleeve and substantially prevent it from tipping over.

Another alternate embodiment provides for the opening and the shoulder to intersect with each other. When a tool is inserted through the opening into the supporting ring, this tool is located in the area of the shoulder and thus in the area in which the inner sleeve is buttressed so the front surface, i.e., the teeth of the inner sleeve, can be directly accessed.

A preferred variation provides for the diameter of the opening to be greater than the thickness of the shoulder. When a tool is inserted through this type of opening, it projects beyond the shoulder and can directly engage the front surface of the sleeve. When the sleeve is fitted with teeth, such as are provided in an alternate embodiment of this disclosure, the portion of the tool that projects beyond the shoulder directly mates with the teeth which project into the inside cross-section of the opening.

As mentioned hereinabove, the teeth can be designed in the form of a bevel gear so that the bevel gear, in association with a mating pinion gear tool having a complementary tooth pitch, result in a bevel gear pinion drive system. This has the advantage that, without the need of reinserting the tool, the inner sleeve can be very sensitively turned inside the outer sleeve, with any turning positions being possible. Thus, the inner sleeve does not have to be turned to a certain position in order to be able, e.g., to remove or reinsert the tool.

The inner sleeves and the outer sleeves preferably have a right-hand thread or a left-hand thread. This has the advantage that the same components can be used for the two inner sleeves; this also applies to the outer sleeves if no special adjustment to the position or shape of the vertebrae is necessary. Furthermore, only one tool or one machine setting is required to produce the inside thread on the outer sleeve and to produce the outside thread on the inner sleeve.

To substantially ensure an optimum union between the implant and the surrounding tissue, the surface of the inner sleeves and/or the outer sleeves has perforations through which the growth of bone tissue is facilitated. In addition, the perforations also reduce the overall weight of the implant.

According to an alternate embodiment, at least one of the perforations of at least one of the sleeves is of a size that makes it possible to fill or to supplement the sleeve with tissue substance. After the spinal implant according to the present disclosure has been extended, this implant first is generally filled with additional tissue substance which can easily be inserted via relatively large perforations. These relatively large perforations are also located in the surface of at least one of the sleeves, with the perforations preferably having an elongated or a long oval shape.

To substantially ensure an optimum fit of the spinal implant to the curvature of the spinal column, at least one of the outer sleeves has a front surface which projects outwardly and which is located at an angle to the orthogonal plane relative to the longitudinal axis. Thus, this outside surface does not run perpendicular to the longitudinal axis of the spinal implant but is inclined relative to this plane. Since the system is a modular system, there are a number of different outer sleeves to choose from, which sleeves have outside surfaces with different angles of inclination, or surfaces with no inclination.

These outside surfaces preferably have spinous extensions so that an optimum support on the abutting vertebra is substantially ensured.

To fix the final extended position, the outer sleeve and the associated inner sleeve can be affixed to each other by means of a set (grub) screw that can be radially screwed into the outer sleeve. This substantially ensures that the spinal implant does not independently change its position, in particular that it does not contract.

To connect the two inner sleeves to each other, a locking element is provided, which locking element maintains the two inner sleeves on the supporting ring, with the locking element having outwardly projecting detents, in particular on elastic tabs, which extend behind inwardly projecting shoulders provided on the inner sleeve. An additional advantage of this locking element is that the entire spinal and implant can be modularly constructed and can be assembled immediately prior to implantation. No tools are required since the locking element needs to be merely pushed into an inner sleeve and be extended behind the shoulders of the adjacent inner sleeve.

The subject matter of the present disclosure also relates to a tool for adjusting the extendable spinal implant, the tool being designed in the shape of a rod and having a star-shaped cross-section. In addition, the distal end of the tool can be slightly conically tapered similar to a beveled gear. The tool can be easily inserted into and turned in the supporting ring. In addition, the tool can be disposed on a flexible shaft so that the implant can be used and extended even if it is difficult to access the implant.

The extendable spinal implant according to the present disclosure will be described more specifically immediately below.

FIG. 1 shows a preferred embodiment of a spinal implant in its compressed state, designated generally as 10. One can see an upper outer sleeve 12 and a lower outer sleeve 14 which, with their front surfaces 16 (see FIG. 2) facing each other, rest against a supporting ring 18. In addition, one can see that outer sleeves 12 and 14 have perforations 20 through which bone tissue can grow into the inside of the spinal implant 10.

Supporting ring 18 has radially running openings 22, through the inside cross-section 24 of which portions of teeth 26 can be seen. Also, the two outer sleeves 12 and 14 have outwardly oriented front surfaces 28 and 30 which have spinous extensions 32 that project in axial direction. These spinous extensions 32 penetrate the contact surfaces of the neighboring vertebrae and there anchor the two outer sleeves 12 and 14.

Figure 2:
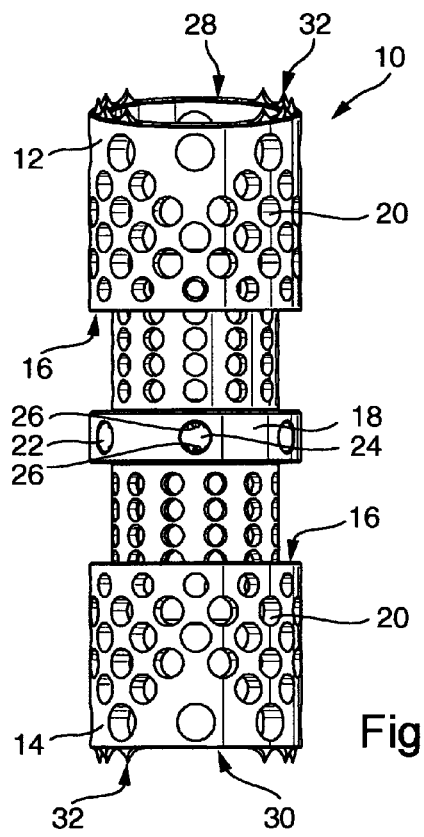
FIG. 2 is a perspective view of the spinal implant of FIG. 1 in an extended position.
Figure 3:
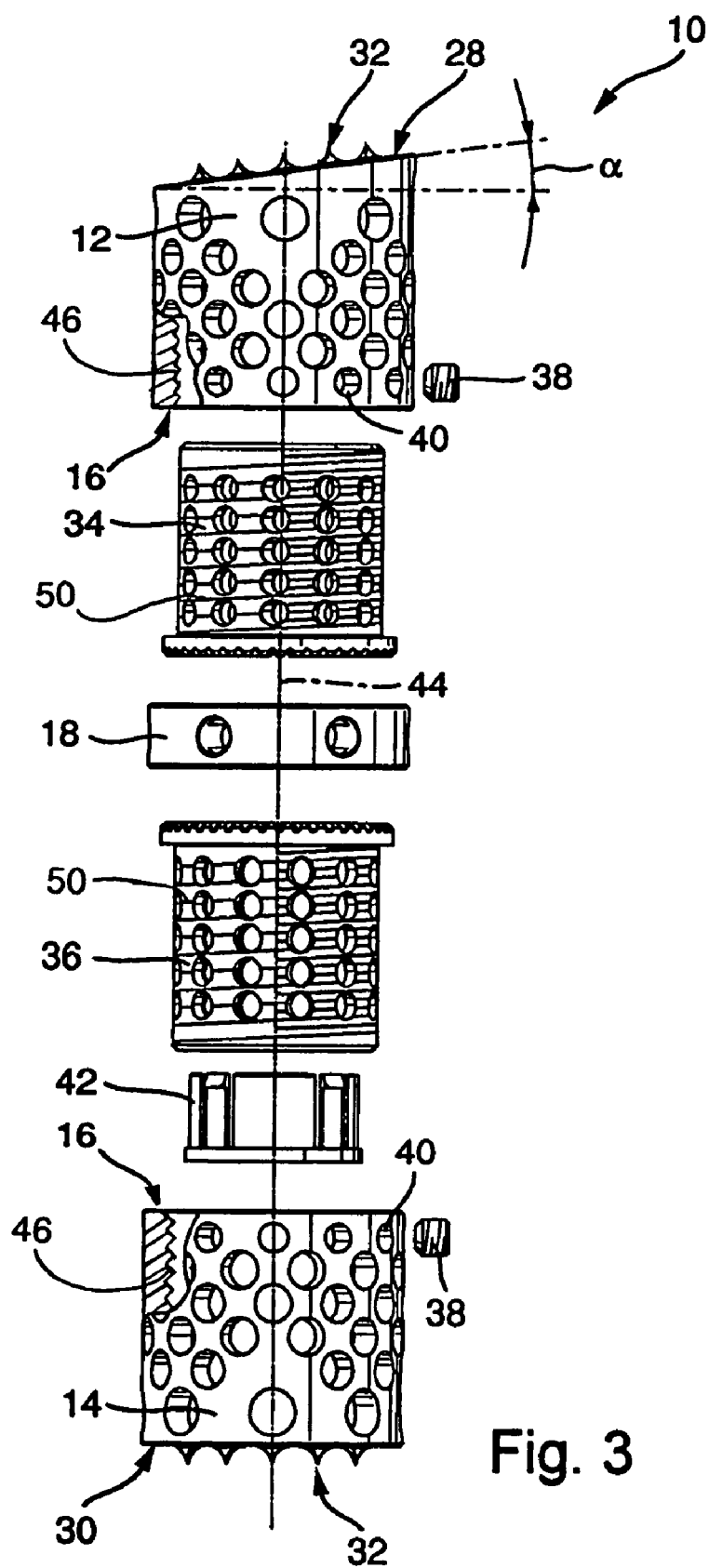
FIG. 3 is an exploded perspective, partially cutaway and partially cross-sectional view of the spinal implant of FIG. 1.

FIGS. 2 and 3 show an upper inner sleeve 34 and a lower inner sleeve 36 which are screwed into the associated upper outer sleeve 12 and lower outer sleeve 14. In addition, the figures show two set (grub) screws 38 which can be screwed into an associated tapped hole 40 of outer sleeves 12 and 14, which affixes outer sleeves 12 and 14 to inner sleeves 34 and 36. Tapped holes 40 for set screws 38 are located in the immediate vicinity of front surfaces 16 of outer sleeves 12 and 14. Also visible is a locking element 42 by means of which the two inner sleeves 34 and 36 can be attached to each other.

One can clearly see that the plane of front surface 28 is inclined at an angle α to the orthogonal plane relative to longitudinal axis 44. This makes it possible to optimally adjust spinal implant 10 to the position of the neighboring vertebrae or to correct the position of said vertebrae. For this purpose, an outer sleeve 12 or 14 having a front surface 28 or 30, respectively, with the inclination required is selected. It can also be seen that sleeves 12, 14, 34, and 36 and supporting ring 18 and locking element 42 are disposed coaxially with respect to one another and with respect to longitudinal axis 44.

Figure 4:
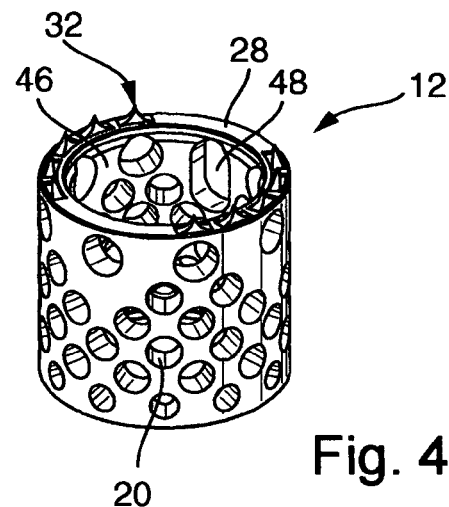
FIG. 4 is an enlarged perspective view of the upper outer sleeve of FIG. 3.
Figure 5:
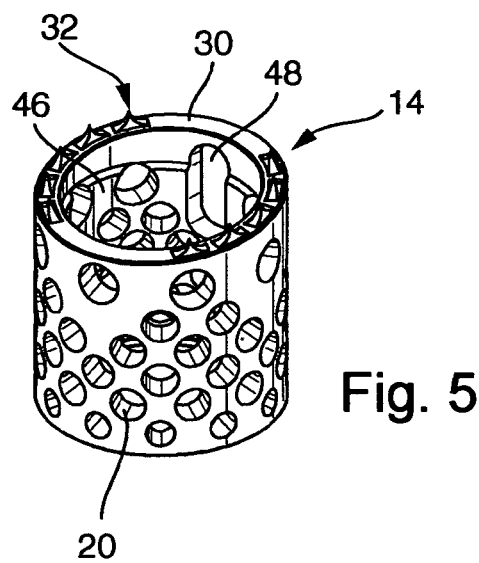
FIG. 5 is an enlarged perspective view of the lower outer sleeve of FIG. 3.

FIGS. 4 and 5 are enlarged representations of the two outer sleeves 12 and 14, except that the inside thread 46 disposed on the inner circumference is only schematically shown or suggested. The inside threads 46 are shown in FIG. 3. This inside thread 46 is, e.g., a fine thread with a pitch of 1 mm and a diameter of 22 mm, and is designed as a right-hand thread.

FIGS. 4 and 5 also show that a relatively large oblong perforation 48 is provided in the walls of outer sleeves 12 and 14. After extensions, bone tissue can be filled into the inside of spinal implant 10 through perforation 48.

Figure 6:
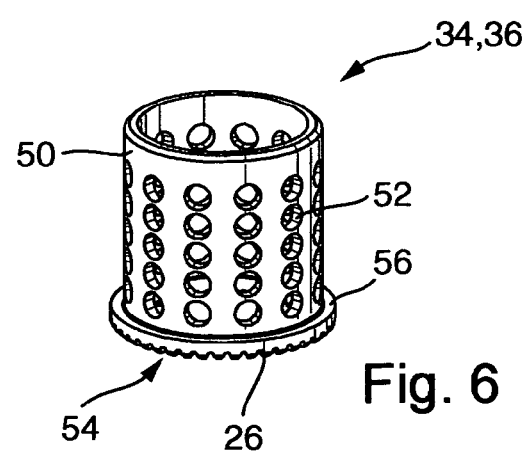
FIG. 6 is an enlarged perspective view of an inner sleeve.
Figure 7:
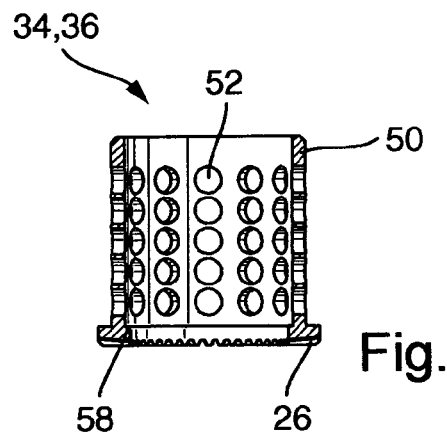
FIG. 7 is a longitudinal cross-sectional view through the inner sleeve.

FIG. 6 shows an enlarged perspective view of inner sleeves 34 and 36 which, along their outer circumference, have an outside thread 50 which again is only schematically shown or suggested. Outside thread 50 is shown in FIG. 3. Inner sleeves 34 and 36 also have perforations 52. On one of their front surfaces 54, inner sleeves 34 and 36 have a flange 56 which projects radially outwardly and which, on its outwardly oriented front surface, has teeth 26 which are preferably designed in the form of beveled teeth. In the longitudinal section shown in FIG. 7, these beveled teeth can be clearly seen.

Figure 9:
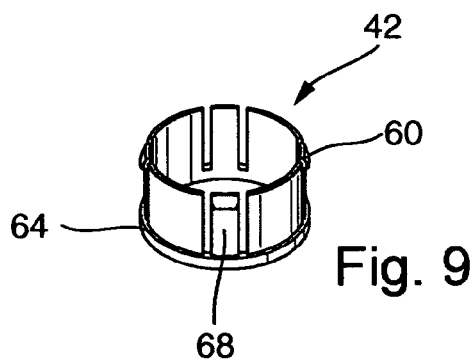
FIG. 9 is an enlarged perspective view of a locking element.

It can also be seen that flange 56 has a shoulder 58 which projects radially inwardly and onto which detents 60 of a locking element 42 can latch. Such a locking element 42 is shown in FIG. 9. This locking element 42 is also designed in the form of a sleeve and has, on its surface lying oppositely to detents 60, a radially projecting retention flange 64 which comes to lie behind the associated shoulder 58 of the other inner sleeve 36. The detents are disposed on elastic tabs 68, thus making it possible to deflect them radially toward the inside. In this manner, it is possible to connect the two inner sleeves 34 and 36 to each other.

Figure 8:
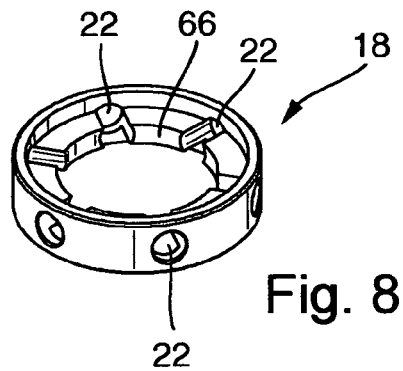
FIG. 8 is an enlarged perspective view of a supporting ring.

FIG. 8 shows supporting ring 18 on which the two inner sleeves 34 and 36 with teeth 26 are seated. For this purpose, supporting ring 18 has a shoulder 66 which projects radially inwardly and which is subdivided into a total of six segments. Shoulder 66 is disposed in such a way as to intersect with openings 22, with the diameter of openings 22 being greater than the thickness of shoulder 66. This has the effect that part of teeth 26 project into the inside cross-section of openings 22 when inner sleeves 34 and 36 are resting on shoulder 66. Teeth 26 can thus be accessed from the outside through opening 22, as shown in FIGS. 1 and 2.

Figure 10:
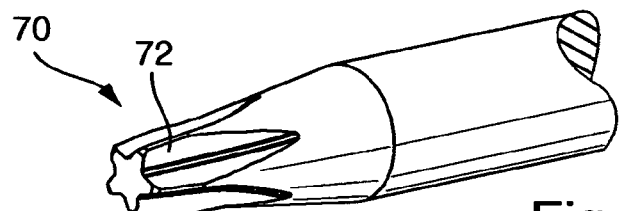
FIG. 10 is a cutaway, perspective view of a tool for extending the spinal implant of the present disclosure.

FIG. 10 finally shows a tool 70 which has an oblong shape and a star-shaped cross-section. Tool 70 also has teeth 72 which, together with teeth 26, form a bevel tooth gear. The tool can be disposed on a right rod or on a flexible shaft, thus making it easily possible for tool 70 to reach even difficult-to-access areas and to extend spinal implant 10.

While several embodiments have been described in detail, it will be apparent to those skilled in the art that the disclosed embodiments may be modified. Therefore, the foregoing description is to be considered exemplary rather than limiting.

What is claimed is:

1. An extendable spinal implant, comprising:
   a first outer sleeve;
   a second outer sleeve coaxially disposed to the first outer sleeve;
   an inside drive element having two opposed ends, one of the two opposed ends of the inside drive element screwed to at least one of the first and second outer sleeves, the inside drive element having an outside thread, and the at least one of the first and second outer sleeves having an inside thread threadingly engageable with the outside thread, the inside drive element further including two inner sleeves; and
   a supporting ring upon which an other of the two opposed ends of the inside drive element is rotatably seated, the inside drive element adapted to be rotatably driven with respect to the supporting ring at the other of the two opposed ends of the inside drive element.

2. The spinal implant as defined in claim 1 wherein each of the two inner sleeves is screwed into one of the first and second outer sleeves.

3. The spinal implant as defined in claim 1 wherein the inner sleeves are spaced a certain distance apart by means of the supporting ring.

4. The spinal implant as defined in claim 1 wherein at least one of the other of the two opposed ends of the inside drive element and the inner sleeves has teeth.

5. The spinal implant as defined in claim 1 wherein the supporting ring has at least one radial opening.

6. The spinal implant as defined in claim 1 wherein the supporting ring has a shoulder which projects radially inwardly, the shoulder supporting the other of the two opposed ends of the inside drive element.

7. The spinal implant as defined in claim 6 wherein the supporting ring has at least one radial opening, and wherein the opening and the shoulder intersect with each other.

8. The spinal implant as defined in claim 7 wherein the diameter of the opening is greater than the thickness of the shoulder.

9. The spinal implant as defined in claim 1 wherein each of the inner sleeves and the first and second outer sleeves has a right-hand thread or a left-hand thread.

10. The spinal implant as defined in claim 1 wherein at least one of the inner sleeves and the first and second outer sleeves has perforations.

11. The spinal implant as defined in claim 10 wherein at least one of the perforations of at least one of the inner sleeves and the first and second outer sleeves is large enough to enable the filling of the at least one of the inner sleeves and the first and second outer sleeves with tissue substance.

12. The spinal implant as defined in claim 1 wherein one of the first and second outer sleeves has an outwardly projecting front surface which is positioned at an angle (α) to the orthogonal plane relative to the longitudinal axis.

13. The spinal implant as defined in claim 1 wherein one of the first and second outer sleeves and the associated inner sleeve are adapted to be affixed to each other by means of a set screw that can be radially screwed into the outer sleeve.

14. The spinal implant as defined in claim 1 wherein the two inner sleeves are maintained on the supporting ring by means of a locking element, with the locking element having outwardly projecting detents which extend behind inwardly projecting shoulders that are disposed on the inner sleeves.

15. An extendable spinal implant, comprising:
   a first outer sleeve;
   a second outer sleeve coaxially disposed to the first outer sleeve;
   an inside drive element having two opposed ends, one of the two opposed ends of the inside drive element screwed to at least one of the first and second outer sleeves, the inside drive element having an outside thread, and the at least one of the first and second outer sleeves having an inside thread threadingly engageable with the outside thread; and a supporting ring upon which an other of the two opposed ends of the inside drive element is rotatably seated, the inside drive element adapted to be driven with respect to the supporting ring at the other of the two opposed ends of the inside drive element;

wherein the inside drive element comprises two inner sleeves, wherein at least one of the other of the two opposed ends of the inside drive element and the inner sleeves has teeth, wherein the supporting ring has at least one radial opening, and wherein the teeth project into an inside cross-section of the opening.

* * * * *